United States Patent
Chi-Wang Chan et al.

(10) Patent No.: US 6,825,296 B2
(45) Date of Patent: Nov. 30, 2004

(54) CATALYST COMPONENT FOR OLEFIN POLYMERIZATION

(75) Inventors: Michael Chi-Wang Chan, Hong Kong (HK); Ka-Ho Tam, Kowloon (HK)

(73) Assignee: The University of Hong Kong, Hong Kong (HK)

( * ) Notice: Subject to any disclaimer, the term of this patent is extended or adjusted under 35 U.S.C. 154(b) by 0 days.

(21) Appl. No.: 10/402,816

(22) Filed: Mar. 28, 2003

(65) Prior Publication Data

US 2003/0191015 A1 Oct. 9, 2003

Related U.S. Application Data

(60) Provisional application No. 60/368,634, filed on Mar. 29, 2002.

(51) Int. Cl.$^7$ .................................................. C08F 4/44
(52) U.S. Cl. ...................... 526/161; 526/171; 526/172; 502/155; 502/167
(58) Field of Search ................................ 526/161, 171, 526/172; 502/155, 167

(56) References Cited

U.S. PATENT DOCUMENTS

| 4,452,914 A | 6/1984 | Coleman, III et al. |
| 5,064,802 A | 11/1991 | Stevens et al. |

(List continued on next page.)

FOREIGN PATENT DOCUMENTS

| EP | 0 606 125 B1 | 5/1997 |
| JP | 6192330 | 7/1994 |
| JP | 9012582 | 1/1997 |
| WO | WO 87/02370 | 4/1987 |

OTHER PUBLICATIONS

Organic Syntheses, Coll. vol. 4 (1963).

(List continued on next page.)

*Primary Examiner*—Robert D. Harlan
(74) *Attorney, Agent, or Firm*—Dickstein, Shapiro, Morin & Oshinsky, LLP.

(57) ABSTRACT

Disclosed herein are compounds shown as Formula I:

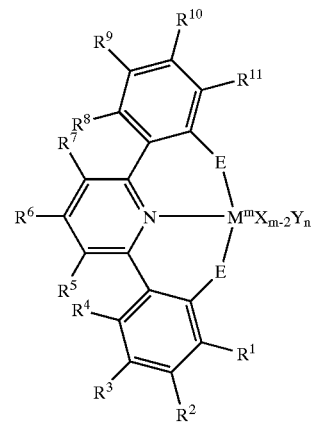

wherein $R^1$–$R^{11}$ are each independently selected from a group comprising hydrocarbyl, substituted hydrocarbyl, heterohydrocarbyl, and substituted heterohydrocarbyl containing 1 to 20 carbon atoms and two or more of the $R^1$–$R^{11}$ groups may be joined to form cyclic versions; $R^1$–$R^{11}$ can also be selected from hydrogen, halogen, and recognized donor and acceptor groups; E is a Group 16 element (including oxygen); M is a metal selected from the group comprising Group 3 to 10 elements (including titanium and zirconium) and the Lanthanide series elements; m is the oxidation state of the metal; X is a monovalent atom or group bonded to M; Y is a mono- or bidentate molecule datively bound to M, and n is zero or an integer up to five. These catalysts, when combined with a suitable activator, are active for the polymerization of olefins.

9 Claims, 2 Drawing Sheets

X-ray crystal structure of the pyridine-bis(phenolate) zirconium Complex 1.

U.S. PATENT DOCUMENTS

| | | | |
|---|---|---|---|
| 5,079,205 | A | 1/1992 | Canich |
| 5,599,761 | A | 2/1997 | Turner |
| 5,637,660 | A | 6/1997 | Nagy et al. |
| 5,840,646 | A | 11/1998 | Katayama et al. |
| 5,852,146 | A | 12/1998 | Reichle et al. |
| 6,020,493 | A | 2/2000 | Liu |
| 6,034,190 | A | 3/2000 | Katayama et al. |
| 6,333,423 | B1 | 12/2001 | Kol et al. |

OTHER PUBLICATIONS

Dietrich–Buchecker et al., entitled "Templated Synthesis of Interlocked Macrocyclic Ligands, The Catenands. Preparation and Characterization of the Prototypical bis=30 Membered Ring System", *Tetahedron*, vol.:46, No. 2, pp. 503–512 (1990).

Holligan et al., entitled "The Co–Ordination Chemistry of Mixed Pyridine–Phenol Ligands; Spectroscopic and Redox Properties of Mononuclear Ruthenium Complexes with (Pyridine)$_{6-x}$(Phenolate)$_x$ Donor Sets (X=1 or 2)", *J. Chem. Soc. Dalton Trans.* Issue 1, pp xx–xxv (1992).

Silva et al., entitled "Synthesis and Molecular Structure of New O/N/O Ligands: *BIS*–Phenol–Pyridine and *BIS*–Phenol–Pyrazole", *Tetahedron*, vol.:53, No. 34, pp. 11645–11658 (1997).

Bei et al., entitled "Synthesis, Structures, Bonding, and Ethylene Reactivity of Group 4 Metal Alkyl Complexes Incorporating 8–Quinolinolato Ligands", *Organometallics* 16, pp. 3282–3302 (1997).

Tuskahara et al., entitled "Neutral and Cationic Zirconium Benzyl Complexes Containing Bidentate Pyridine–Alkoxide Ligands. Synthesis and Olefine Polymerization Chemistry of (pyCR$_2$O)$_2$Zr(CH$_2$Ph)$_2$ and (pyCR$_2$O)$_2$ Zr(CH$_2$pH)$^-$ Complexes", *Organometallics*, 16, pp. 3303–3313 (1997).

Mack et al., entitled "A Pyridine Dialkoxide Titanium Dichloride Complex.. Synthesis and Molecular Structure of 2,6–*bis*(2, 2–Diphenyl–2–Trimethylsilyloxy–Ethyl)Pyridine", *J. Chem. Soc. Dalton Trans.* pp. 917–921 (1998).

Shao, et al., entitled "Dibenzylzirconium Complexes of Chelating Aminodiolates. Synthesis, Structural Studies, Thermal Stability, and Insertion Chemistry", *Organometallics* 19, pp. 509–520 (2000).

Tshuva et al., entitled "Novel Zirconium Complexes of Amine *BIS*(Phenolate) Ligands. Remarkable Reactivity in Polymerization of HEX–1–ENE Due to an Extra Donor Arm", *Chem. Commun.*, pp. 379–380 (2000).

Nakayama et al., entitled "Titanium Complexes Having Chelating Diaryloxo Ligands Bridged by Tellurium and Their Catalytic Behavior in the Polymerization of Ethylene", *Organometallics*, 19. pp. 2498–2503 (2000).

Tsuva et al., entitled "Living Polymerization and Block Copolymerization of α–0Olefins by an Amine *BIS*(Phenolate) Titanium Catalyst", *Chem. Commun.* pp. 2120–2121 (2001).

X-ray crystal structure of the pyridine-bis(phenolate) zirconium Complex 1.

X-ray crystal structure of the pyridine-bis(phenolate) titanium Complex 4.

CATALYST COMPONENT FOR OLEFIN POLYMERIZATION

This application claims the benefit of provisional application 60/368,634 filed Mar. 29, 2002.

FIELD OF INVENTION

This invention relates to a non-metallocene catalyst system, consisting of a pyridine-containing metal compound and a suitable activator, which is highly active in the olefin polymerization process.

BACKGROUND OF THE INVENTION

Polyolefins have been made chiefly using conventional Ziegler catalyst systems, which typically consist of a transition metal halide compound and one or more organoaluminum halide compound. While these catalysts are inexpensive, they suffer from many problems including low activity, staining and instability from residual catalysts, broad molecular distribution, and ineffective co-monomer incorporation. In recent years, the replacement of Ziegler catalysts by metallocene-based systems has begun. Metallocene catalysts, which are transition metal (especially titanium and zirconium) compounds bearing one or more cyclopentadienyl [Cp] ring ligand(s), are typically used with aluminoxanes as activators to give very high activities. Metallocene polyolefin catalysts provide solutions to many of the problems encountered for Ziegler catalysts and are well known in the art.

The commercialization of metallocene catalysts for olefin polymerization has resulted in great interest in the design of non-metallocene homogeneous catalysts. A new generation of catalysts may display superior activity and offer an easier route to known polyolefins and may also lead to processes and products that are outside the capability of metallocene catalysts. In addition, substituted analogues of non-cyclopentadienyl ligands and compounds may be relatively easy to synthesize and hence non-metallocene catalysts may be more economical.

Multidentate anionic oxygen- and nitrogen-based groups have attracted attention as ligands for non-metallocene polyolefin catalysts. In terms of bidentate ligands, pyridinoxy and quinolinoxy ligands have been reported (e.g. U.S. Pat. Nos. 5,637,660, 5,852,146, 6,020,493; Bei et al, *Organometallics* 1997, 17, 3282; Tshukahara et al, *Organometallics* 1997, 17, 3303).

A series of tetradentate anionic ligands containing amine-bis(phenolate) groups (phenolate is an aromatic hydroxyl group) have recently been applied in polyolefin catalysts by Kol, Goldschmidt and coworkers (U.S. Pat. No. 6,333,423, Tshuva et al, *Chem. Commun.* 2000, 379 and *Chem. Commun.* 2001, 2120). However, these disclosures state that the fourth coordinating moiety or extra donor arm is essential for highly active catalysts, and compounds without the donor arm show poor catalytic activity. In addition, these disclosures focus on the polymerization of 1-hexene, and no information on the polymerization of lower olefins is given. Shao et al (*Organometallics* 2000, 19, 509) describe zirconium complexes of chelating amine-bis(alkoxide) (alkoxide is an aliphatic hydroxyl group) as polyolefin catalysts, but the observed activity is very low.

Polyolefin catalysts with at least one phenolate group are well known in the art (U.S. Pat. Nos. 4,452,914, 5,079,205). U.S. Pat. Nos. 5,840,646, 6,034,190, EP 0 606 125, and WO 87/02370 disclose bidentate bis(phenolate) titanium and zirconium catalysts for olefin polymerization. Japan Unexamined Patent 6-192330 describes bis(phenolate) plus pyridine-bis(alkoxide) titanium and zirconium catalysts. Further examples of pyridine-bis(alkoxide) groups as ligands in Group 4 metal polyolefin catalysts have been disclosed (JP 9-012582 and Mack et al, *J. Chem. Soc. Dalton. Trans.* 1998, 917), but the observed activities for the polymerization of ethylene are only moderate.

Hence there is a need in the art for new olefin polymerization catalysts, particularly catalysts containing multidentate ligands of the pyridine-phenolate type. There is also a need in the art for new polyolefin catalysts containing unsymmetric ligands, because this may result in the stereoselective polymerization of 1-olefins (alpha-olefins) and give polyolefins with distinctive morphology and properties.

SUMMARY OF THE INVENTION

This invention relates to a polyolefin catalyst system, which comprises a Group 3 to 10 or lanthanide metal (including titanium and zirconium) compound bearing a tridentate pyridine-containing ligand and a suitable activator.

This invention also relates to non-metallocene catalysts of Formula I shown below:

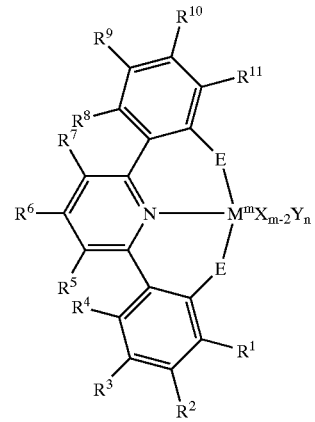

wherein $R^1$–$R^{11}$ are each independently selected from a group comprising hydrocarbyl, substituted hydrocarbyl, heterohydrocarbyl, and substituted heterohydrocarbyl containing 1 to 20 carbon atoms and two or more of the $R^1$–$R^{11}$ groups may be joined to form cyclic versions; $R^1$–$R^{11}$ can also be selected from hydrogen, halogen, and recognized donor and acceptor groups; E is a Group 16 element (including oxygen); M is a metal selected from the group comprising Group 3 to Group 10 elements (including titanium and zirconium) and the Lanthanide series elements; m is the oxidation state of the metal; X is a monovalent atom or group bonded to M; Y is a mono- or bidentate molecule datively bound to M, and n is zero or an integer up to five. These catalysts, when combined with a suitable activator, are active for the polymerization of olefins. In instances where $R^1$–$R^{11}$ are selected such that the tridentate [ENE] ligand is unsymmetric, stereoselective polymerization of 1-olefins can be achieved.

DETAILED DESCRIPTION OF THE INVENTION

Figure 1:
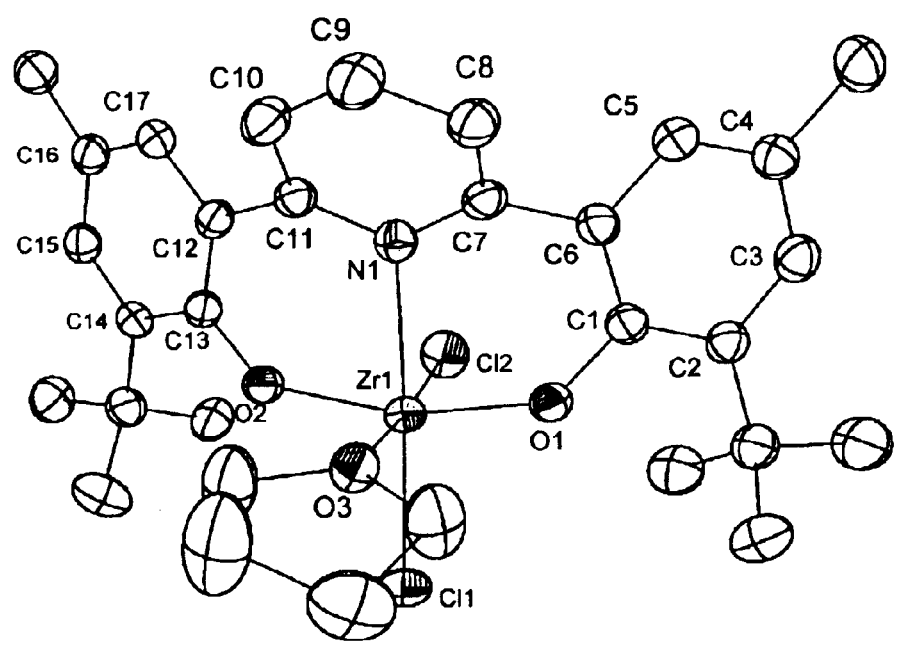
FIG. 1 is an illustration of the X-ray crystal structure of the pyridine-bis(phenolate) zirconium Complex 1.

This invention relates to a polyolefin catalyst system, which comprises a Group 3 to 10 or lanthanide metal (including titanium and zirconium) compound bearing a tridentate pyridine-containing ligand and a suitable activator.

This invention also relates to non-metallocene catalysts of Formula I shown below:

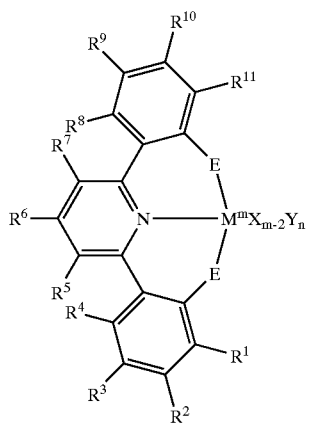

I wherein $R^1$–$R^{11}$ are each independently selected from the group consisting of hydrogen, halogen, recognized donor and acceptor groups, hydrocarbyl, substituted hydrocarbyl, heterohydrocarbyl, and substituted heterohydrocarbyl containing 1 to 20 carbon atoms and two or more of the $R^1$–$R^{11}$ groups may be joined to form cyclic versions; E is a Group 16 (also known as Group VI B) element (including oxygen); M is a metal selected from the group consisting of Group 3 to Group 10 elements (including titanium and zirconium) and the Lanthanide series elements; m is the oxidation state of the metal; X is a monovalent atom or group bonded to M; Y is a mono- or bidentate molecule datively bound to M, and n is zero or an integer up to five. These catalysts, when combined with a suitable activator, are active for the polymerization of olefins.

In one embodiment for the polyolefin catalyst of Formula I, the groups $R^1$–$R^5$ and $R^7$–$R^{11}$ are independently selected to give the following: $R^1$=$R^{11}$, $R^2$=$R^{10}$, $R^3$=$R^9$, $R^4$=$R^8$, and $R^5$=$R^7$. This means that the tridentate ligand is symmetric. In another embodiment, the groups $R^1$–$R^5$ and $R^7$–$R^{11}$ are independently selected to give one of the following or combinations thereof: $R^1 \neq R^{11}$ (that is, $R^1$ is not equal to $R^{11}$), $R^2 \neq R^{10}$, $R^3 \neq R^9$, $R^4 \neq R^8$, $R^5 \neq R^7$. This means that the tridentate ligand is unsymmetric and stereoselective polymerizations can be achieved.

In an exemplary embodiment for the polyolefin catalyst of Formula I, M is selected from the group consisting of titanium and zirconium and E is oxygen such that a tridentate pyridine-bis(phenolate) ligand is coordinated to M.

In a preferred embodiment for the polyolefin catalyst of Formula I, X is selected from a halide group (including chloride) and an alkyl group (including benzyl), and Y is absent or can be selected from the group consisting of neutral O-donor, P-donor and N-donor molecules. Examples of an O-donor molecule that can form a dative bond to M include ethers (e.g. tetrahydrofuran, diethyl ether), and ketones (e.g. acetophenone, benzophenone). Examples of a P-donor molecule that can form a dative bond to M include $PR^aR^bR^c$, wherein $R^{a-c}$ are each independently selected from the group consisting of hydrogen, halogen, recognized donor and acceptor groups, hydrocarbyl, substituted hydrocarbyl, heterohydrocarbyl, and substituted heterohydrocarbyl containing 1 to 20 carbon atoms (e.g. trimethylphosphine, triethylphosphine, dimethylphenylphosphine).

The preparation of the desired ligands can be achieved by modifications of procedures described in the literature. For example, symmetric pyridine-2,6-di(phenol) substrates are prepared by reaction of Grignard reagents derived from oxygen-protected substituted phenols with 2,6-dibromopyridine. Deprotection is accomplished using molten pyridinium chloride. The procedure for the synthesis of unsymmetric pyridine-2,6-di(phenol) substrates is adapted from Silva et al (*Tetrahedron* 1997, 53, 11645), which describes the synthesis of 2,6-di(2'-hydroxyphenyl)pyridine and involves the addition of two 2'-methoxyacetophenone molecules. In this invention, where two different substituted 2'-methoxyacetophenones are used followed by demethylation, then the resultant pyridine-2,6-di(phenol) substrate is unsymmetric.

Metallation of the substituted pyridine-2,6-di(phenol) substrates containing acidic protons can be accomplished by reaction with basic metal reagents such as tetrabenzylzirconium(IV) and titanium(IV) tetrachloride, with elimination of toluene and hydrogen chloride respectively. Alternatively, ligands can be deprotonated with reagents such as n-butyl lithium, then treated with metal halides such as zirconium tetrachloride. The resultant metal complex contains one pyridine-2,6-di(phenolate) ligand which is chelated in a tridentate meridional fashion. A neutral O- (for example tetrahydrofuran or diethyl ether), P- (for example trialkylphosphine or triarylphosphine), or N-donor solvent or substrate is added to the reaction mixture to facilitate the isolation of the complex, in some instances in its solvated/adduct form. As determined by $^1$H NMR spectroscopy and in some case by X-ray crystallography, the two remaining halide ligands are in a cis conformation, and this is important for the employment of these complexes as polyolefin catalysts.

This invention relates to a catalyst system that comprises the metal catalyst and an activator. Generally, the activator converts the complex to a cationic active species. Suitable activators are well known in the art. Examples include trimethylaluminum (TMA), triethylaluminum (TEA), triisobutylaluminum (TIBA), tri-n-octylaluminum, methylaluminum dichloride, ethylaluminum dichloride, dimethylaluminum chloride, diethylaluminum chloride, aluminoxanes, and the like. Aluminoxanes are known in the art as typically the oligomeric compounds that can be prepared by the controlled addition of water to an alkylaluminum compound, for example trimethylaluminum. Examples of aluminoxanes compounds include methylaluminoxane (MAO), modified methylaluminoxane (MMAO), ethylaluminoxane, and diisobutylaluminoxane. In this invention, alkylaluminoxanes such as methylaluminoxane (MAO) are preferred.

Mixtures of alkylaluminoxanes and trialkylaluminum compounds are particularly preferred, such as MAO with TMA or TIBA. In this context it should be noted that the term "alkylaluminoxane" as used in this specification includes alkylaluminoxanes available commercially which may contain a proportion, typically about 10 wt %, but optionally up to 50 wt %, of the corresponding trialkylaluminum; for instance, commercial MAO usually contains approximately 10 wt % trimethylaluminum (TMA), whilst commercial MMAO contains both TMA and TIBA. Quantities of alkylaluminoxane quoted herein include such trialkylaluminum impurities, and accordingly quantities of trialkylaluminum compounds quoted herein are considered to comprise compounds of the formula $AlR_3$ additional to any $AlR_3$ compound incorporated within the alkylaluminoxane when present.

Suitable activators also include acid salts that contain non-nucleophilic anions. These compounds generally consist of bulky ligands attached to boron or aluminum. Examples include lithium tetrakis(pentafluorophenyl) borate, dimethylphenylammonium tetra(pentafluorophenyl) borate, trityl tetra(pentafluorophenyl)borate, and the like. Suitable activators also include trialkyl or triarylboron compounds such as tris(pentafluorophenyl)boron, tris (pentabromophenyl)boron, and the like. Other suitable activators are described, for example, in U.S. Pat. Nos. 5,064, 802, and 5,599,761.

In the preparation of the catalysts of the present invention, the quantity of the activator to be employed is determined by testing. It is found that the quantity employed is 0.1 to 20,000 atoms, preferably 1 to 2000 atoms of aluminum or boron per metal compound molecule, particularly when an aluminoxane activator is used.

In a preferred embodiment, one or more of the polyolefin catalyst of Formula I is combined with one or more of the activators named above or a mixture thereof to form a catalyst system that is active for the olefin polymerization process.

The catalysts and catalyst systems are especially valuable for the polymerization, including homopolymerization and copolymerization, of olefins. Suitable olefins include one or more of ethylene, propylene, butenes, pentenes, hexenes, octenes, styrenes, 1,3-butadiene, norbornene, and the like or combinations thereof. Preferred olefins are ethylene, propylene, and mixtures thereof with 1-olefins such as 1-butene, 1-hexene, and 1-octene. In one embodiment, a homopolymer of ethylene is produced.

The catalyst system of the present invention can also include one of more other transition metal compounds, such as conventional Ziegler catalysts, metallocene catalysts, constrained geometry catalysts, or heat-activated supported chromium oxide (e.g. Phillips-type) catalysts.

The catalysts and catalyst system are used with or without an inorganic solid or organic polymer support. Suitable supports include silica, alumina, magnesia, titania, clays, zeolites, polymeric supports such as polyethylene, polypropylene, polystyrene, functionalized polystyrene and the like. The supports can be pretreated thermally or chemically to improve catalyst productivity or product properties. The catalysts and/or activators can be deposited on the support in any desired manner. For instance, the catalyst can be dissolved in a solvent, combined with a support, and stripped. Alternatively, an incipient-wetness technique can be used. Moreover, the support can simply be introduced into the reactor separately from the catalyst.

The catalysts can be used in a variety of well-known olefin polymerization processes, including gas, high-pressure liquid, slurry, bulk, solution, or suspension-phase techniques, and combinations of these. The liquid phase process comprises the steps of contacting an olefin monomer with the catalyst system in a suitable polymerization solvent and reacting said monomer in the presence of said catalyst system for a time and at a temperature and pressure sufficient to produce a polyolefin. The pressures used typically range from about 10 psi to about 15,000 psi. Polymerization temperatures range from about −100° C. to about 300° C., more preferably from about −50° C. to about 200° C., and most preferably from about 0° C. to about 150° C.

The polymerization process of the present invention affords polymers, especially polyethylene, at high productivity. This means that very small quantities of the catalysts are consumed in the polymerization process. This also means that after the polymerization process, the amounts of catalysts or residues in the polymer will be very small such that a catalyst separation step during the polymer recovery process may not be required.

In one embodiment, the activity of the ethylene polymerization process of this invention can be greater than 5 kg of polymer per mmol of catalyst per hour per atmosphere of ethylene, which corresponds to a catalyst turnover frequency (TOF) of greater than $1.8 \times 10^5$ per hour per atmosphere of ethylene. Such high activities and TOF values require highly dilute catalyst solutions to prevent mass transfer-limited rates. An increase in the temperature of the reactor can be observed for polymerization runs after a certain period of time and hence the observed activities will be lower due to the said mass transfer-limited rates. However, under such exothermic conditions, the polymerization process of this invention is long-lived and still produces polymer at high productivity.

At all times, the individual catalyst system components, as well as the catalyst system once formed, are protected from oxygen and moisture. Therefore, the reactions are performed in an oxygen- and moisture-free atmosphere and, where the catalyst system is recovered separately it is recovered in an oxygen and moisture free atmosphere. Preferably, therefore, the reactions are performed in the presence of an inert dry gas such as for example, helium or nitrogen.

The following examples merely illustrate the present invention. Those skilled in the art will recognize many variations that are within the spirit of the invention and scope of the claims.

EXAMPLES

All experiments were performed under a nitrogen atmosphere using standard Schlenk techniques or in a Braun dry-box. $^1$H and $^{13}$C NMR spectra were recorded on a Bruker Avance 600, 500 DRX, 400 or 300 FT-NMR spectrometer (ppm). Mass spectra (EI) were obtained on a Finnigan MAT 95 mass spectrometer. Melting points of the polymers were determined by differential scanning calorimetry on a Perkin Elmer DSC7. Catalyst activities are measured in grams per millimole of catalyst per hour per atm. Methylaluminoxane (MAO, 10 wt % solution in toluene) was purchased from Aldrich (Schlenk, Braun, Bruker, Finnigan, Perkin Elmer and Aldrich are trademarks).

Example 1

1.1. Synthesis of Intermediate 1

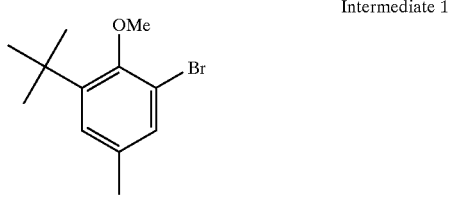

Intermediate 1

Intermediate 1 was prepared according to a general methylation procedure (for example, see: *Org. Synth. Coll. Vol.* 4, 836 (1963)). In a 250 mL round-bottomed flask fitted with a reflux condenser and a calcium chloride guard tube are placed 2-bromo-4-methyl-6-tert-butylphenol (synthesized as in Nakayama et al, *Organometallics* 2000, 19, 2498; 6.3 g, 26 mmol), anhydrous potassium carbonate (3.6 g, 26 mmol) and methyl iodide (2.5 mL, 40 mmol) in 80 mL of acetone. The mixture was allowed to reflux at 60–70° C. for 20 hours. After removing the acetone by distillation, the residual liquid was acidified with dilute sulfuric acid then extracted with dichloromethane (3×30 mL). The combined organic extracts were washed with water and dried over magnesium sulfate. Evaporation of the solvent afforded a yellow oil, which was purified by silica gel flash chromatography using n-hexane:ethyl acetate (50:1) as eluent to give a pale yellow solid. Yield: 6.1 g, 91%.

$^1$H NMR (300 MHz, CDCl$_3$): 1.37 (s, 9, $^t$Bu), 2.25 (s, 3, Me), 3.89 (s, 3, OMe), 7.04 (s, 1, Ar), 7.23 (s, 1, Ar). Positive EI-MS (m/z): 258 [M$^+$].

1.2. Synthesis of Intermediate 2

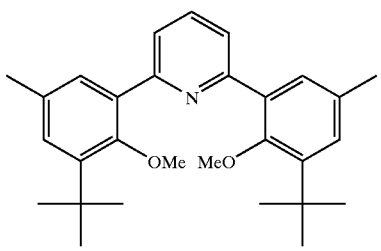

Intermediate 2

Intermediate 2 was prepared by modification of the following literature procedure: Holligan et al, *J. Chem. Soc., Dalton Trans.* 1992, 3345. The required Grignard reagent was prepared by refluxing Intermediate 1 (4.82 g, 18.7 mmol) and magnesium turnings (0.90 g, 37.0 mmol) in tetrahydrofuran (THF, 40 mL) for 2 hours. Upon cooling down to room temperature, the resultant mixture was filtered under N$_2$ and added dropwise to a mixture of 2,6-dibromopyridine (2.02 g, 8.53 mmol) and [Ni(dppe)Cl$_2$] (dppe=Ph$_2$PCH$_2$CH$_2$PPh$_2$, 0.30 g, 0.57 mmol) in dry THF (20 mL) at 0° C. The mixture was allowed to warm up to room temperature, then stirred under reflux for 12 hours. The reaction was then quenched by addition of aqueous ammonium chloride, acidified with HCl and volatiles were removed under reduced pressure. The acidic aqueous solution was washed with dichloromethane, CH$_2$Cl$_2$ (3×20 mL), neutralized with aqueous potassium hydroxide, and extracted with CH$_2$Cl$_2$ (3×20 mL). The combined organic extracts were dried over magnesium sulfate and the solvent was removed to give a red oil. Purification was performed by silica gel flash chromatography using n-hexane:ethyl acetate (9:1) as eluent to give a orange-yellow solid. Yield: 2.8 g, 77%.

$^1$H NMR (300 MHz, CDCl$_3$): 1.43 (s, 18, $^t$Bu), 2.36 (s, 6, Me), 3.37 (s, 6, OMe), 7.15 (s, 2, Ar), 7.42 (s, 2, Ar), 7.68–7.76 (m, 3, py). Positive EI-MS (m/z): 431 [M$^+$].

1.3. Synthesis of Intermediate 3

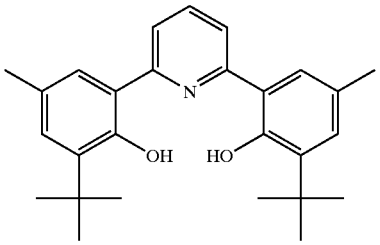

Intermediate 3

Demethylation of Intermediate 2 (3.0 g, 6.96 mmol) in molten pyridinium chloride (12.0 g, 104 mmol) under N$_2$ at 210° C. for 10 hours according to the procedure described by Dietrich-Buchecker et al (*Tetrahedron* 1990, 46, 503) gave Intermediate 3 as a pale yellow solid which can be recrystallized in n-hexane. Yield: 1.6 g, 57%.

$^1$H NMR (300 MHz, CDCl$_3$): 1.45 (s, 18, $^t$Bu), 2.35 (s, 6, Me), 7.18 (s, 2, Ar), 7.30 (s, 2, Ar), 7.62 (d, 2, J=8.0 Hz, py-H$^{3,5}$), 7.96 (t, 1, J=8.0 Hz, py-H$^4$), 10.52 (br s, 2, OH). Positive EI-MS (m/z): 403 [M$^+$].

1.4. Synthesis of Complex 1

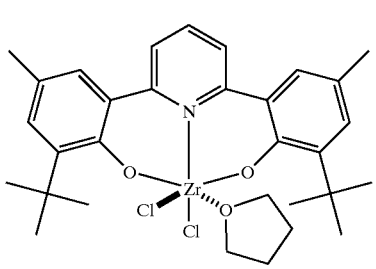

Complex 1

A solution of n-butyl lithium (0.70 mL, 2.5 M) in hexane was added at −78° C. to Intermediate 3 (0.345 g, 0.86 mmol) in toluene (25 mL). The yellow solution was stirred for 1 hour at room temperature, then slowly added at −78° C. to zirconium(IV) tetrachloride (0.200 g, 0.86 mmol) in toluene (15 ml) and tetrahydrofuran (THF, 8 mL). The resultant yellow solution was stirred for 1 hour at −78° C. and for 12 hours at room temperature. Filtration and concentration of the mixture gave a pale yellow solid, which was recrystallized from toluene to yield large yellow crystals. Yield: 0.39 g, 66%. The X-ray crystal structure for Complex 1 has been determined (FIG. 1).

$^1$H NMR (500 MHz, C$_6$D$_6$): 0.76 (br, 4, thf), 1.79 (s, 18, $^t$Bu), 2.22 (s, 6, Me), 3.46(br, 4, thf), 6.81 (s, 2, Ar—H$^6$), 7.01–7.04 (t, 1, J=7.6 Hz, py-H$^4$), 7.09–7.11 (d, 2, J=7.6 Hz, py-H$^{3,5}$), 7.34 (s, 2, Ar-H$^4$). Positive EI-MS (m/z): 563 (100%) [M$^+$-thf].

Example 2

Synthesis of Complex 2

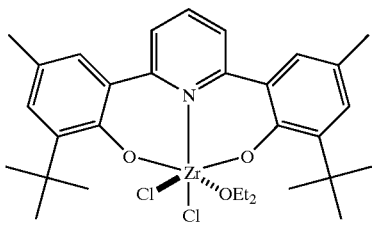

Complex 2

The procedure for the synthesis of Complex 1 was adopted using diethyl ether instead of toluene and tetrahydrofuran as reaction solvent. A pale yellow solid was obtained in 55% yield.

$^1$H NMR (300 MHz, $C_6D_6$): 0.93 (br, 6, $Et_2O$), 1.78 (s, 18, $^tBu$), 2.20 (s, 6, Me), 3.28–3.35 (br q, 4, $Et_2O$), 6.78 (s, 2, Ar—H$^6$), 7.09–7.18 (m, 3, py-H$^{3-5}$), 7.33 (s, 2, Ar—H$^4$).

Example 3

Synthesis of Complex 3

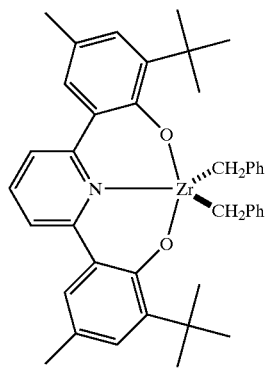

Complex 3

A solution of Intermediate 3 (0.230 g, 0.57 mmol) in diethyl ether (15 mL) was slowly added to tetrabenzylzirconium(IV) (0.260 g, 0.57 mmol) in diethyl ether (15 mL) at −78° C. The resultant mixture was stirred for 30 minutes at −78° C. and for 10 hours at room temperature to give a bright yellow cloudy solution. Filtration, concentration and storage of the solution at −78° C. for 12 hours gave a bright yellow crystalline solid. Yield: 0.24 g, 62%.

$^1$H NMR (600 MHz, $C_6D_6$): 1.74 (s, 18, $^tBu$), 2.27 (s, 6, Me), 2.67 (s, 4, $CH_2$), 6.5–6.61 (t, 2, J=7.3 Hz, Ph-H$^4$), 6.75–6.77 (m, 6, Ph-H$^3$ and Ar—H$^6$), 6.79–6.81 (t, 1, J=7.6 Hz, py-H$^4$), 6.91–6.93 (d, 2, J=7.8 Hz, py-H$^{3,5}$), 7.00–7.01 (d, 4, J=7.3 Hz, Ph-H$^2$), 7.35 (s, 2, Ar—H$^4$).

Example 4

Synthesis of Complex 4

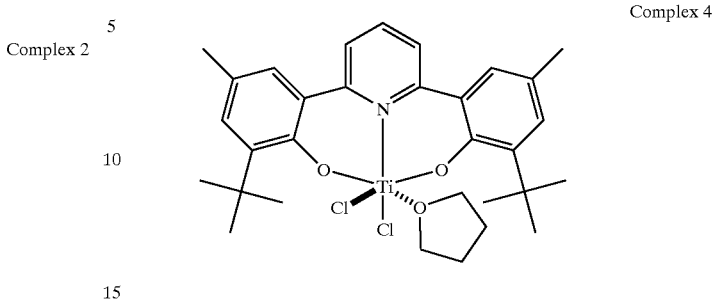

Complex 4

Figure 2:
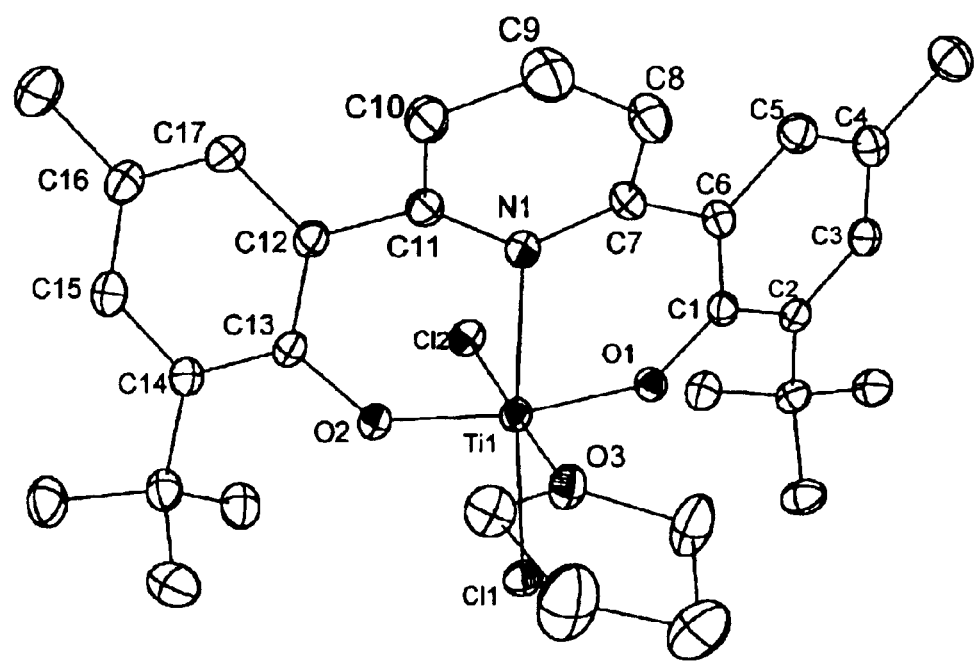
FIG. 2 is an illustration of the X-ray crystal structure of the pyridine-bis(phenolate) titanium Complex 4.

A solution of Intermediate 3 (0.420 g, 1.04 mmol) in diethyl ether (15 mL) and tetrahydrofuran (5 mL) was slowly added to tetrachloro-bis(tetrahydrofuran)titanium (IV) (0.348 g, 1.04 mmol) in diethyl ether (10 mL) and tetrahydrofuran (10 mL) at −78° C. The resultant mixture was stirred for 10 minutes at −78° C. and for 1 hour at room temperature. This resulted in the formation of a dark red solution and precipitation of a dark red microcrystalline solid, which was collected and dried under vacuum. Yield: 0.51 g, 83%. The X-ray crystal structure for Complex 4 has been determined (FIG. 2).

$^1$H NMR (400 MHz, $C_6D_6$): 0.87 (br, 4, thf), 1.88 (s, 18, $^tBu$), 2.23 (s, 6, Me), 3.41 (br, 4, thf), 6.93 (s, 2, Ar—H$^6$), 7.03–7.07 (t, 1, J=7.9 Hz, py-H$^4$), 7.19–7.21 (d, 2, J=7.9 Hz, py-H$^{3,5}$), 7.34 (s, 2, Ar—H$^4$). Positive EI-MS (m/z): 519 (100%) [M$^+$-thf].

Example 5

5.1. Synthesis of Intermediate 4

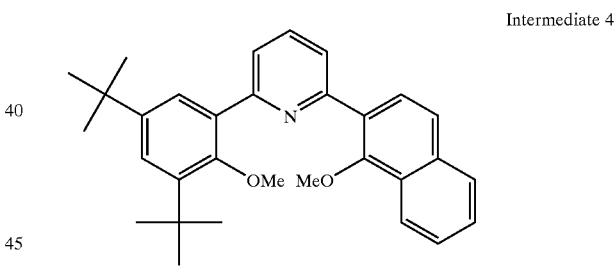

Intermediate 4

Intermediate 4 was prepared by modification of the following literature procedure: Silva et al, *Tetrahedron* 1997, 53, 11645. A solution of 3,5-di-tert-butyl-2-methoxyacetophenone (3.12 g, 12 mmol) and potassium tert-butoxide (2.71 g, 24 mmol) in tetrahydrofuran (THF, 15 mL) was stirred for 2 hours at room temperature to give a yellow suspension. A solution of 1-N,N-dimethylamino-3-(2'-methoxynaphthyl)-3-oxo-1-propene (prepared from 1-methoxy-2-acetonaphthone by modification of Silva et al, *Tetrahedron* 1997, 53, 11645; 3.05 g, 12 mmol) in THF (20 mL) was then added and the mixture was stirred for 12 hours at room temperature to give a dark red solution. A solution of ammonium acetate (9.18 g, 119 mmol) in acetic acid (60 mL) was added to the mixture. THF was removed by distillation over 2 hours and the residue was dried under vacuum. Dichloromethane (30 mL) was added to yield a red solution, which was neutralized with saturated sodium bicarbonate solution then extracted with $CH_2Cl_2$ (3×20 mL). The combined organic extracts were washed with water and brine, dried over sodium sulfate and the solvent was removed to give a red oil. Purification was performed by silica gel flash chromatography using n-hexane:ethyl acetate (20:1) as eluent to give a pale yellow solid. Yield: 1.9 g, 68%.

$^1$H NMR (300 MHz, CDCl$_3$): 1.37 (s, 9, $^t$Bu), 1.45 (s, 9, $^t$Bu), 3.40 (s, 3, Ome), 3.77 (s, 3, Ome), 7.40 (s, 1, Ar), 7.52–7.56 (m, 2, Nap), 7.63 (s, 1, Ar), 7.73–7.89 (m, 4, py and Nap), 8.03–8.12 (m, 2, py and Nap), 8.25–8.28 (d, 1, J=8.4 Hz, Nap).

5.2. Synthesis of Intermediate 5

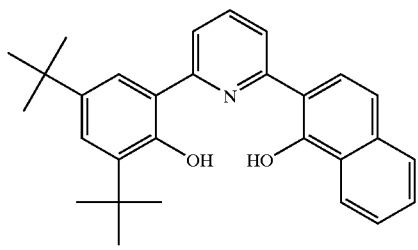

Intermediate 5

Demethylation of Intermediate 4 (1.91 g, 4.21 mol) in molten pyridinium chloride (10.0 g, 86.5 mol) under N$_2$ at 220° C. for 10 hours according to the procedure described by Dietrich-Buchecker et al (*Tetrahedron* 1990, 46, 503) gave Intermediate 5 as a pale yellow solid which can be recrystallized in n-hexane. Yield: 1.12 g, 63%.

$^1$H NMR (400 MHz, C$_6$D$_6$): 1.37 (s, 9, $^t$Bu), 1.65 (s, 9, $^t$Bu), 7.04–7.09, 7.27–7.32, 7.42–7.48, 7.63–7.66 (m, 10, Ar), 8.72–8.75 (d, 1, J=8.4 Hz, Ar), 9.50 (br s, 1, OH), 12.78 (br s, 1, OH). Positive EI-MS (m/z): 425 [M$^+$].

5.3. Synthesis of Complex 5

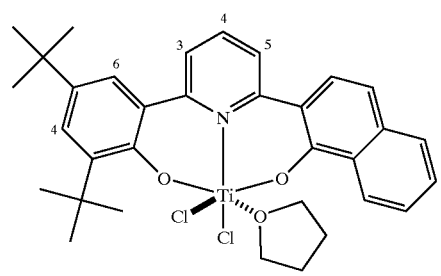

Complex 5

The procedure for the synthesis of Complex 4 was adopted using Intermediate 5 instead of Intermediate 3. Addition of n-hexane to the dark red reaction mixture resulted in the precipitation of a dark red microcrystalline solid, which was collected and dried under vacuum. Yield: 69 %.

$^1$H NMR (500 MHz, C$_6$D$_6$): 0.78 (br, 4, thf), 1.33 (s, 9, 5-$^t$Bu), 1.88 (s, 9, 3-$^t$Bu), 3.37 (br, 4thf), 7.07–7.11 (t, 1, J=7.9 Hz, py-H$^4$), 7.24–7.25 (d, 1, J=7.5 Hz, py-H$^3$), 7.27–7.34 (m, 4, Nap), 7.47–7.49 (d, 1, J=7.8 Hz, py-H$^5$), 7.52 (s, 1, Ar—H$^6$), 7.59–7.60 (d, 1, J=7.2 Hz, Nap), 7.73 (s, 1, Ar—H$^4$), 9.08–9.10 (d, 1, J=8.0 Hz, Nap). Positive EI-MS (m/z): 541 (100%) [M$^+$-thf].

Polymerization Tests

The polymerization tests described below were carried out using the following procedure. Ethylene polymerization was carried out under atmospheric pressure in toluene in a 100 mL glass reactor containing a magnetic stir bar. Toluene (40 mL) was introduced into the reactor containing the catalyst and stirred. This solution was submerged in a liquid bath of the required polymerization temperature for 30 minutes and purged with ethylene for 15 minutes. Polymerization was initiated by adding a toluene solution of methylaluminoxane (MAO), and the reactor was maintained under 1 atmosphere (atm) of ethylene for the duration of the polymerization. After the prescribed time, HCl-acidified methanol (40 mL) was added to terminate the polymerization, and the ethylene gas feed was stopped. The resultant solid polymer was collected by filtration, washed with acidified methanol and dried in vacuum to constant weight.

Example 6

Using Complex 1 (3 mg, 4.72 µmol) as catalyst with MAO (4.7 mL, 7.08 mmol of a 10 wt % solution in toluene; 1500 equivalents) activator, ethylene polymerization was carried out at 20° C. for 20 minutes. The yield of the isolated polymer was 5.42 g, which corresponds to an activity of 3448 g/mmol h atm, and the melting point of the polymer was 126.7° C.

Example 7

Using Complex 1 (3 mg, 4.72 µmol) as catalyst with MAO (3.1 mL, 4.72 mmol of a 10 wt % solution in toluene; 1000 equivalents) activator, ethylene polymerization was carried out at 20° C. for 6 minutes. The yield of the isolated polymer was 3.32 g, which corresponds to an activity of 7029 g/mmol h atm, and the melting point of the polymer was 127.0° C.

Example 8

Using Complex 1 (2 mg, 3.15 µmol) as catalyst with MAO (4.2 mL, 6.29 mmol of a 10 wt % solution in toluene; 2000 equivalents) activator, ethylene polymerization was carried out at 20° C. for 5 minutes. The yield of the isolated polymer was 2.07 g, which corresponds to an activity of 7880 g/mmol h atm, and the melting point of the polymer was 125.4° C.

Example 9

Using Complex 1 (3 mg, 4.72 mmol) as catalyst with MAO (3.1 mL, 4.72 mmol of a 10 wt % solution in toluene; 1000 equivalents) activator, ethylene polymerization was carried out at 1° C. for 2 minutes. The yield of the isolated polymer was 0.23 g, which corresponds to an activity of 1447 g/mmol h atm, and the melting point of the polymer was 134.0° C.

Example 10

Using Complex 1 (3 mg, 4.72 mmol) as catalyst with MAO (3.1 mL, 4.72 mmol of a 10 wt % solution in toluene; 1000 equivalents) activator, ethylene polymerization was carried out at 65° C. for 2 minutes. The yield of the isolated polymer was 0.31 g, which corresponds to an activity of 1987 g/mmol h atm, and the melting point of the polymer was 111.0° C.

Example 11

Synthesis of Complex 6

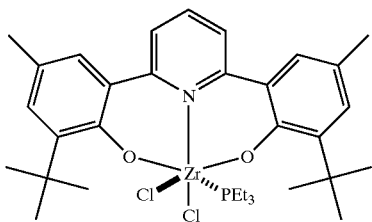

Complex 6

A solution of Intermediate 3 (0.200 g, 0.50 mmol) in toluene (20 mL) was slowly added to zirconium bisbenzyl dichloride [Zr(CH$_2$Ph)$_2$Cl$_2$(Et$_2$O)(dioxane)$_{0.5}$] (0.230 g, 0.50 mmol) and excess triethylphosphine (PEt$_3$) in 20 mL toluene at −78° C. The resultant mixture was stirred for 10 minutes at −78° C. and for 5 hours at room temperature to give a yellow solution containing a pale yellow precipitate. The yellow solid was collected and recrystallized using a mixture of dichloromethane and hexane to afford a pale yellow crystalline solid, which was dried under vacuum. Yield: 0.24 g, 71%.

$^1$H NMR (500 MHz, CD$_2$Cl$_2$): 1.21 (dt, 9, J=19.9, 7.7 Hz, PCH$_2$CH$_3$), 1.55 (s, 18, $^t$Bu), 2.18 (br, 6, PC$\underline{H}_2$CH$_3$), 2.33 (s, 6, Me), 7.09 (s, 2), 7.22 (s, 2), 7.73 (d, 2, J=7.9 Hz, py-H$^{3,5}$), 7.97 (t, 1, J=7.9 Hz, py-H$^4$). $^{31}$P NMR (162 MHz, CD$_2$Cl$_2$): 20.36. Positive EI-MS (m/z): 563 [M$^+$-PEt$_3$].

Example 12

Using Complex 6 (8 mg, 12.2 mmol) as catalyst with MAO (4.0 mL, 6.1 mmol of a 10 wt % solution in toluene; 500 equivalents) activator, ethylene polymerization was carried out at 1° C. for 10 minutes. The yield of the isolated polymer was 2.76 g, which corresponds to an activity of 1358 g/mmol h atm, and the melting point of the polymer was 132.7° C.

As is apparent from the previous general description and the specific embodiments, while forms of the invention have been illustrated and described, various modifications can be made without departing from the scope and spirit of the invention. Accordingly, it is not intended that the invention be limited thereby.

A number of references have been cited and the entire disclosures of which are incorporated herein by reference.

What is claimed is:

1. A polyolefin in catalyst component comprising non-metallocene catalysts of Formula I:

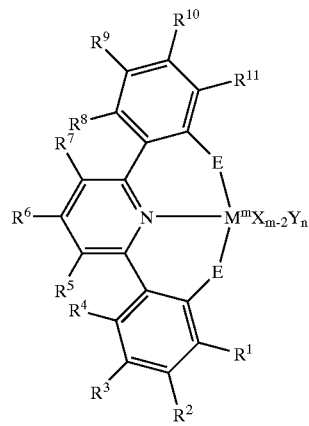

wherein R$^1$–R$^{11}$ are each independently selected from the group consisting of hydrogen, halogen, hydrocarbyl, substituted hydrocarbyl, heterohydrocarbyl, and substituted heterohydrocarbyl containing 1 to 20 carbon atoms and two or more of the R$^1$–R$^{11}$ groups may be joined to form cyclic versions;
E is a Group 16 element
M is a metal selected from the group comprising of Group 3 to Group 10 elements and the Lanthanide series elements;
m is the oxidation state of the metal;
X is a monovalent atom or group bonded to M;
Y is a mono- or bidentate molecule datively bound to M; and
n is zero or an integer up to five.

2. The polyolefin catalyst component according to claim 1, wherein the groups R$^1$–R$^5$ and R$^7$–R$^{11}$ are independently selected to give the following: R$^1$=R$^{11}$, R$^2$=R$^{10}$, R$^3$=R$^9$, R$^4$=R$^8$, and R$^5$=R$^7$.

3. The polyolefin catalyst component according to claim 1, wherein the groups R$^1$–R$^5$ and R$^7$–R$^{11}$ are independently selected to give one of the following or combination thereof: R$^1$≠R$^{11}$, R$^2$≠R$^{10}$, R$^3$≠R$^9$, R$^4$≠R$^8$ and R$^5$≠R$^7$.

4. The polyolefin catalyst component according to claim 1, wherein M is selected from the group consisting of titanium and zirconium.

5. The catalyst component according to claim 1, wherein E is oxygen.

6. The polyolefin catalyst component according to claim 1, wherein X is selected from the group consisting of halide and alkyl.

7. The polyolefin catalyst component according to claim 1, wherein Y is selected from the group consisting of neutral O-donor molecules.

8. The polyolefin catalyst component according to claim 1, wherein Y is selected from the group consisting of neutral P-donor molecules.

9. The polyolefin catalyst component according to claim 1, wherein Y is absent or selected from the group consisting of neutral N-donor molecules.

* * * * *